United States Patent
Hissink et al.

(10) Patent No.: US 8,187,254 B2
(45) Date of Patent: May 29, 2012

(54) BIODEGRADABLE DRAINS FOR MEDICAL APPLICATIONS

(75) Inventors: Catharina Everdina Hissink, Groningen (NL); Rob Steendam, Groningen (NL); Linda Joan Gibcus, Groningen (NL); Johan Zuidema, Groningen (NL)

(73) Assignee: Polyganics B.V. (NL)

( * ) Notice: Subject to any disclaimer, the term of this patent is extended or adjusted under 35 U.S.C. 154(b) by 1013 days.

(21) Appl. No.: 10/532,351

(22) PCT Filed: Nov. 3, 2003

(86) PCT No.: PCT/NL03/00761
§ 371 (c)(1),
(2), (4) Date: Sep. 14, 2005

(87) PCT Pub. No.: WO2004/039424
PCT Pub. Date: May 13, 2004

(65) Prior Publication Data
US 2006/0142736 A1   Jun. 29, 2006

(30) Foreign Application Priority Data
Nov. 1, 2002   (EP) ..................................... 02079560

(51) Int. Cl.
*A61M 1/00* (2006.01)
*A61F 13/00* (2006.01)
(52) U.S. Cl. ....................... 604/540; 424/422
(58) Field of Classification Search .................. 604/540, 604/265, 264, 48, 93.01; 526/317.1
See application file for complete search history.

(56) References Cited

U.S. PATENT DOCUMENTS

| | | | | |
|---|---|---|---|---|
| 3,406,691 A | * | 10/1968 | Kettenbach | 604/93.01 |
| 4,650,488 A | * | 3/1987 | Bays et al. | 623/23.64 |
| 4,719,246 A | * | 1/1988 | Murdoch et al. | 521/134 |
| 4,955,859 A | * | 9/1990 | Zilber | 604/8 |
| 5,017,188 A | * | 5/1991 | Marten et al. | 604/178 |
| 5,026,378 A | * | 6/1991 | Goldsmith, III | 606/109 |
| 5,129,889 A | | 7/1992 | Hahn et al. | 604/265 |
| 5,201,724 A | | 4/1993 | Hukins et al. | 604/265 |
| 5,466,444 A | * | 11/1995 | Jurgens | 424/78.08 |
| 5,468,253 A | * | 11/1995 | Bezwada et al. | 606/230 |
| 5,599,291 A | * | 2/1997 | Balbierz et al. | 604/8 |
| 5,599,552 A | * | 2/1997 | Dunn et al. | 424/423 |
| 5,681,873 A | * | 10/1997 | Norton et al. | 523/115 |
| 5,713,920 A | * | 2/1998 | Bezwada et al. | 606/230 |
| 6,669,711 B1 | * | 12/2003 | Noda | 606/196 |
| 2002/0013546 A1 | * | 1/2002 | Grieshaber et al. | 604/28 |
| 2003/0105245 A1 | * | 6/2003 | Amsden | 525/450 |
| 2003/0134811 A1 | * | 7/2003 | Jackson et al. | 514/44 |

FOREIGN PATENT DOCUMENTS
FR   2825281 A1 * 12/2002

* cited by examiner

*Primary Examiner* — Tatyana Zalukaeva
*Assistant Examiner* — Susan Su
(74) *Attorney, Agent, or Firm* — Banner & Witcoff, Ltd.

(57) ABSTRACT

The invention relates, generally, to medical appliances. More particularly, it relates to tubular shaped devices used as drains for draining fluids (liquids and/or gases) from antrums or other parts of the human or animal body. According to the present invention a drain is provided, which is suitable for draining a human or animal antrum, which drain comprises a synthetic biodegradable material, preferably a biodegradable polymer.

23 Claims, 1 Drawing Sheet

BIODEGRADABLE DRAINS FOR MEDICAL APPLICATIONS

The invention relates, generally, to medical appliances. More particularly, it relates to tubular shaped devices used as drains for draining fluids (liquids, viscous substances and/or gases) from antrums or other parts of the human or animal body.

In both human and veterinary medicine, it is often desirable to get access to an antrum in order to discharge pus or other material which may form as a result of inflammatory conditions. This is for instance the case with (chronic) sinusitis or inflammatory conditions in the middle ear.

Chronic sinusitis symptoms can be difficult to treat, in part because treatment may require the coordinated efforts of several specialists to treat all of the aspects of the disease. Chronic sinusitis can be broken down into bacterial chronic sinusitis and non-infectious chronic sinusitis. Both have different medical treatment options. Many people with non-infectious chronic sinusitis respond to topically or orally administered steroids or nasal wash treatments.

Depending on the severity of the sinusitis, there are several treatments to consider such as antibiotics and sinus surgery. Sinus surgery is generally a last line of defense for doctors to relieve a sinusitis condition. In this type of surgery the natural opening to the sinuses is enlarged. The procedure includes removal of areas of obstruction, with the aim of reinstating the normal flow of mucus.

Unfortunately the newly created opening or connection between the sinus and the nasal cavity has the tendency to re-narrow (restenose) necessitating a re-intervention. Therefore, sinus-nasal stents, drains or cannula's have been developed to further improve the result of the drainage procedure. U.S. Pat. No. 4,737,141 discloses a method to drain the maxillary sinus with a temporary biodurable plastic drain, by placing the drain in an artificially created opening in the maxillary cavity, which method is an improvement of the classical treatment with multiple lavages of the antrum.

However, a drawback of the currently available drains is that they need to be removed in due time. Removal of these drains may damage the new drainage tract causing it to re-occlude. Moreover, the procedure is time-consuming and unpleasant for the patient.

In a majority of cases the drains according to the state of the art are left in place only for a short period of time before they are removed. However, in some cases it is desirable to leave the drain in place for a longer period of time e.g. because the antrum, surrounding tissue or anatomical structure needs more time to heal. Known nasal drainage tubes may be left in place for as long as 6 months or more to drain an antrum.

Leaving these known drains in place for a long period of time may lead to complications. The materials used for known drains (usually plastic) may induce irritation but may also induce an inflammatory response. Inflammatory responses may lead to the formation of scar tissue, which in it self, may require treatment, especially when this occurs in the natural drainage pathway of an antrum. Furthermore, removal of these devices may traumatize the surrounding tissue due to mechanical forces and since newly formed tissue may have attached firmly to the device, it is also possible that the tissue grows attached to the device and pulling it free may consequently damage the tissue.

Apart from the application in draining fluids or gases from antrums, drains are also applied to drain fluids or viscous substances from organs or tissue. In surgically operated areas a drain is left behind for several days to drain the tissue fluid. Also drains can be applied directly to organs if the effluent of that organ can not by drained via the natural route. Sometimes drains become blocked or occluded so that they have to be removed or replaced. Especially when the drain has to be applied for a longer period of time it may become fixed in the body, making removal very difficult or even impossible and not without discomfort and risk for the patient.

Disorders in the colon and esophagus such as inflammation, carcinomas, diverticulitis, perforation, etc., frequently require resection of a segment of the intestine. After the resection, the proximal and distal sections of the intestine are reconnected, which operation is known as anastomosis. Anastomotic dehiscence or leakage is one of the major problems associated with coloanal anastomoses in the middle or lower rectum, or anastomoses in the esophagus. A temporary colostomy may be placed to reduce the risk of leakage by giving time to intestinal healing, but the construction and closure thereof is associated with a high morbidity and mortality. Instead of placing a temporary colostomy, a protective drain can be placed as an inner lining of the intestines to protect the wound and the interior of the body cavity from contamination with the intestinal contents and to promote healing of the wound. The contents of the colon or esophagus (feces or food, respectively) may then pass in a natural way.

U.S. Pat. No. 4,719,916 and U.S. Pat. No. 4,905,693 disclose an intra-intestinal bypass graft of a thin walled latex or silastic tube. It is placed as a lining to protect the intestinal mucosa from contact with food and/or feces. The graft is stapled or sutured to the mucosa and passes from the body naturally after a certain period of time. A disadvantage is that the disappearance of the graft has to be proven by X-ray. A bio-fragmentable ring made of polyglycolic-acid has been used to make a sutureless anastomosis. The use of this ring is described in various publications among which German patent DE-A-40 42 248 and is commercially available under the name 'Valtrac™'. However, fast degradation of glycolic-acid may cause severe tissue reactions. Furthermore, the ring is brittle and stiff which may cause restenosis of the lumen so that the natural peristaltic motions are suspended.

U.S. Pat. No. 5,129,889 describes an epidural catheter made of a synthetic biodegradable polymer, used for repeated or continual injections of anesthetic agents. The catheter has no drainage function. It mentions homopolymers of cyclic monomers, such as dioxanone and caprolactone; polylactide; polyglycolide; copolymers of glycolide and lactide; copolymers of a cyclic monomer, such as $\epsilon$-caprolactone and glycolide or lactide as suitable materials for the catheter. There is, however, little information on suitable compositions of such polymers in U.S. Pat. No. 5,129,889.

U.S. Pat. No. 5,201,724 describes a catheter for bodily fluids, in particular for urine, consisting of a tube of a non-biodegradable conventional flexible material such as NR, PVC, PU, PTFE and silicone rubber. To this supporting tube of conventional material there is applied a layer of a biodegradable material, which hydrolyses in the urinary fluids to give acidic degradation products. The biodegradable materials mentioned in U.S. Pat. No. 5,201,724 are polylactides, polyglycolides and polybutyrates. This known catheter does not solve the above-mentioned problems associated with subsequent removal of the catheter.

U.S. Pat. No. 4,650,488 discloses prosthetic devices formed of biodegradable material useful as an ear ventilation tube and for draining otitis media from the middle ear. These known prosthetic devices are to retain at least some structural integrity.

The device is based on, for example, poly(DL-Lactide), poly(DL-lactide-co-glycolide) or poly(caprolactone). The polymers have a monomer composition that results in a stiff material at body conditions.

U.S. Pat. No. 2,593,980 (1952) discloses a surgical drainage tube which is absorbable by the human system and provided with a plurality of perforations on one end. It is not specifically used for draining antrums, but it is mentioned that the drain can be inserted e.g. through the mouth into the stomach. The biodegradable material is preferably catgut, a naturally occurring material (collagen).

Biodegradable materials originating from a natural source, for example Type I collagen, hyaluronic acid derivatives, polysaccharides and chitosan, have been used in various medical applications. These biomaterials have some disadvantages e.g. the properties of natural polymers are difficult to control; they may have batch to batch variations, and they are generally more expensive than synthetic materials. Also, biodegradable material of natural sources, especially of animal origin, is not preferred to be used, because of the biological hazards associated with its use. Synthetic materials usually do not suffer from these disadvantages.

Accordingly there is a need for a novel, temporary drain, which drain is flexible and remains functional in the body or antrum orifice for the duration of the prescribed, clinical appropriate period of time to accomplish the predetermined therapeutic purpose.

It was found that this can be obtained by providing drains made from a biodegradable synthetic material having a phase transition temperature of at most mammalian body temperatures (which is generally 37° C. for humans). Thus, the present invention relates to a drain suitable for draining a human or animal antrum, organ or tissue characterized in that it comprises a biodegradable synthetic material. The biodegradable material is preferably a biodegradable synthetic polymer.

A drain is defined herein as a tube, optionally having perforations (in particular pores), which is placed into an antrum, organ or tissue by a natural body orifice or by an artificially created orifice in the wall of an antrum or in an organ or tissue. An "antrum" is defined herein as a natural occurring body cavity which may also be a lumen. The function of the drain is to carry fluids (such as liquids, viscous substances and/or gases). A drain differs from a stent in that stents are used to mechanically support lumen walls (such as in blood vessels or ureteral passages) in case of strictures or obstructions. Stents are designed in a such a way that they can withstand radial stresses. The stent must be non-elastic at body conditions and must therefore be composed of a material with a specific strength and stiffness. These mechanical properties are different from those of drains, which are preferably flexible and elastic. Also, since drains generally do not have to support lumen walls, the resilience may be lower than that of stents. Stents are usually placed in lumens to assist the normal liquid transport in the body (such as blood circulation or urine transport from kidney to bladder). Drains assist the natural channels in the body that carry body fluids, in general from the antrum, organ or tissue to the environment outside the body or to another location in the body. Drains may also perform itself as an artificial channel in the body. Also regarding its degradation behavior, the drains of the present invention differ from biodegradable stents. The degradation of biodegradable stents usually starts and continues from the inner core towards the outer layer. In particular when stents are applied in blood vessels, it is very important that no fragments of partially degraded material are released on the inside of the tube, since this could lead to migration of these fragments through the body, which would be hazardous. In the drains according to the present invention, however, the degradation may commence and propagate on the outside towards the inside or in the bulk, optionally under influence of the fluids that are drained. If fragmentation occurs, this generally does not present any problems, since these fragments are transported to locations (such as the environment or the oral cavity) were they can do no harm. Fragmentation may be even an advantage, since the fragments of the biomaterial can leave the body after the drain has fulfilled its function, without necessarily being re-sorbed by the body.

The drain of the present invention may be essentially cylindrical (viz. having a constant cross-section) or its cross-section may vary in order to suit specific applications, e.g. by providing it with a funnel shaped end, as will be described hereinbelow in more detail. It is also possible according to the present invention to provide a drain that is created in situ in the human or animal body by providing a device with one open end, which is subsequently processed in such a way that it becomes a drain, i.e., a tube with two open ends.

Synthetic biodegradable materials such as polymers have been used for many medical applications that require only a temporary presence of a device in the body. Devices of biodegradable materials are used mainly in tissue repair and drug delivery. These materials can be used as films, sheets, tubes, plugs, pins, rods, fibers, ligaments, scaffolds, microspheres, membranes, and so forth. These products, which can be solid or porous, can have all kind of shapes. Devices of biodegradable material have been used as an implant or in wound closure, as wound dressings, artificial skin or in drug delivery and can be applied in the mucous membrane tissue by insertion via a body orifice e.g. for tissue recovery after a surgical procedure or an injury.

The majority of biocompatible, biodegradable synthetic materials that are being used in medical devices is based on synthetic polyesters made of (mixtures of) cyclic lactones such as glycolide, lactide, ε-caprolactone, para-dioxanone, trimethylenecarbonate and of polyesters made by a condensation reaction of diols and diacids or hydroxyalkanoic acids. These polyesters can be used as such or in combinations with polyethers, polyurethanes, polyamides or with organic or inorganic compounds. A wide range of medical devices has been developed and/or manufactured so far of these types of biomaterials.

WO-A-03/66705 discloses the use of a copolymer of DL-Lactide and ε-caprolactone with a specific composition in the manufacture of a biodegradable nerve guide, which is a flexible, solid tube. A specific monomer composition is required to supply the product with the best performance properties such as mechanical strength, softening temperature and compression modulus.

U.S. Pat. No. B2-6,423,092 discloses a biodegradable stent for implantation in a body lumen made of two layers of a different biomaterial composition, resulting in a different degradation rate if the inner and outer layer. This type of stent is being developed for replacing permanent stents, e.g. for treating stenosis of the lumen in urological applications.

In U.S. Pat. No. 5,085,629 a bioresorbable ureteral stent made of a terpolymer of lactide, glycolide and caprolactone is disclosed.

The materials properties (mechanical, physical and degradation) of the drains of the present invention are different from those of previously described stents or drainage tubes and are specific for application of a biodegradable drain. The properties of the drain according to the present invention will be discussed in more detail in the description of the preferred embodiment.

A drain of a synthetic biodegradable material will have the advantage that it degrades over time where after it is being resorbed and/or excreted by the body. This has the advantage that no additional intervention is required to remove the device, but also that the incidence of adverse events and complications, associated with the removal procedure is reduced. Since the biodegradable drains are similar in design to the conventional biodurable devices, rinsing of the antrum, which is desired in some clinical cases, remains possible.

An example of such a biodegradable drain tube could be the drainage of bile from the liver. This is required in patients where the natural bile secretion pathway has become blocked, e.g. due to tumor growth or liver necrosis.

The drain can be used until it becomes blocked. A biodegradable drain can be used longer than the biodurable version since the biodurable version has to be removed before it becomes occluded and attached in the body. In contrast to conventional biodurable drains, which have to be removed, which action brings patient risk and discomfort, the biodegradable drain according to the present invention is left in place where it degrades and is being absorbed over time. If desired, after some time a new biodegradable drain according to the invention may be placed to take over the function of the previous one.

The use of biodegradable and bio-resorbable materials for manufacturing medical devices having a temporary function is well known and common practice. In general, the use of a biodegradable device may prevent the potential complications associated with biodurable devices when used for both short and longer periods of time.

The present invention provides a device for draining an antrum which is composed of a synthetic biodegradable material and which is easily passed from the body or antrum orifice after a specific therapeutic period of time.

The biodegradable drain of the present invention can be employed for treating frontal and maxillary sinusitis. Preferably the drain has a distal end that is shaped in such a way that it is easily retained in the sinus cavity (anchor). The drain can be inserted through the natural orifice or through a surgically created opening. The drain can be introduced e.g. by the use of a forceps, a guidewire, a trocar or unsupported. The biodegradable drain of the present invention may further be used for draining tear fluid from a nasolacrimal duct.

Furthermore, a biodegradable drain can be applied in the digestive track. Such a drain can be inserted through a natural body orifice e.g. by means of a surgical stapler and can subsequently be fixated to the tissue by stapling.

The biodegradable drain of the present invention may further be used for draining tear fluid from a nasolacrimal duct. The present invention provides drains made of biodegradable synthetic polymeric materials, which degrade with such a rate giving the surrounding tissue time to heal, maintaining an opening of the antrum or lumen and without damaging the surrounding tissue when it degrades. The degradation products of this biocompatible, biodegradable drainage device are cleared either via the digestive channel, the body or antrum orifice or absorbed by the body and metabolized and/or secreted.

Figure 1:
FIG. 1 shows a straight biodegradable drain of the present invention.

The drain according to the present invention, comprises cylindrical tubes (drains) of appropriate sizing (outer diameter: from 0.5-50 mm, total length of 3-300 mm, wall thickness from 0.05-5.0 mm) for being used in draining various antrums or organs. As shown in FIG. 1 the drain can be a hollow tube of substantial length and diameter for being applied as a nasolacrimal duct to temporarily drain the tear fluid where after the tube degrades and the original nasolacrimal duct takes over its function. Straight tubing is, in general, suitable for draining antrums or organs where fixation in the anatomical location by a special tube design is less critical as in the case of the nasolacrimal duct. In the application of a drain in the intestinal tract, it is preferred that the drain is sutured or stapled to the tissue.

Figure 2A:
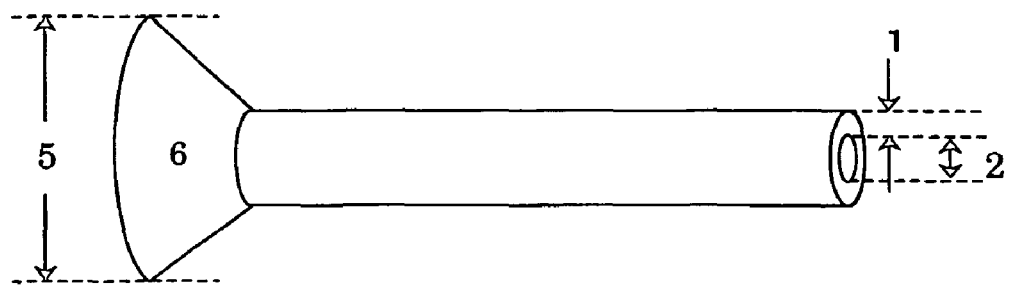
FIG. 2 shows an example of a biodegradable frontal sinus drain of the present invention.
Figure 2B:
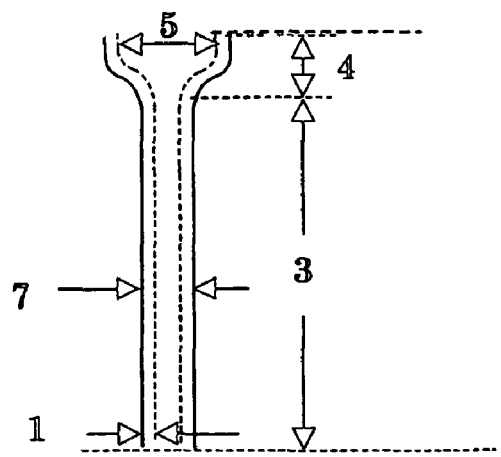

FIG. 2 shows a drain which may be used as a frontal sinus drain in accordance with the present invention, supplied with a funnel (6) at one end of the tube. The drain is characterized by a wall thickness (1), an inner diameter (2), an outer tube diameter (7), a tube length (3), a funnel length (4) and funnel diameter (5). The funnel ensures fixation of the tube in the antrum. This funnel shape is highly preferred over conventional shapes employed for this purpose, such as the "split-end" type of anchoring described in U.S. Pat. No. 4,737,141. It was found that these conventional anchoring means provide for dead spaces or volumes in which stagnant fluid may collect, which in turn form a source of microbiological activity, which may lead to further complications. According to the present invention it is possible to provide anchoring means, such as the funnel shape depicted in FIG. 2, with a smooth and continuous surface, by which these problems can be avoided.

Typically, the tube of FIG. 2 may be used for draining the frontal and/or maxillary sinus. The device can be made out of one piece. The size of the funnel may vary from 3-30 mm in inner diameter and 2-20 mm in length. The dimensions of the cylindrical part are related to each other as in the case of the tube of FIG. 1.

Figure 3:
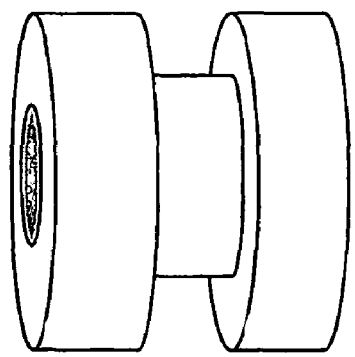
FIG. 3 shows an example of a biodegradable ear vent of the present invention.

Another embodiment of a drain of the present invention is seen in FIG. 3. A cylindrical tube of a single piece, with two flanges, one on each side. A possible application, but not restricted to this, is the drainage of the middle ear. The tube is intended to vent the middle ear and is placed in the tympanic membrane. The tube is placed in an artificially made puncture in the membrane.

The dimensions of the drains and relative dimensions of parts of the drain of FIG. 1-3 will depend on a number of factors, including the anatomy of the patient and the type of surgical procedure.

According to the invention the drain is made of a synthetic biodegradable material. A biodegradable material may be completely resorbed by the body or may degrade by fragmentation of the material. The fragments are cleared either via the digestive channel or via an antrum orifice.

In a more preferred embodiment, the biodegradable material is a synthetic polymer. The polymeric material can be a thermoplastic linear polymer or a thermoset polymer obtainable by cross-linking of (pre)polymers. Examples of synthetic biodegradable polymers that can be applied for manufacturing the drains of the present invention are based on polyesters, polyhydroxyacids, polylactones, polyetheresters, polycarbonates, polydioxanones, polyanhydrides, polyurethanes, polyester(ether)urethanes, polyurethane urea, polyamides, polyesteramides, poly-orthoesters, polyaminoacids, polyphosphonates and polyphosphazenes. The polymeric material may also be composed of mixtures of above components either as different building blocks of the copolymer or cross-linked polymer or as a blend of two or more (co)polymers. Composites of these polymers with organic and inorganic compounds (e.g. radiopaque fillers) are also possible. In addition, the polymer may be loaded with pharmaceutical components such as antibiotics, anti-inflammatory agents, anaesthetics, proteins and many more. The polymer can be loaded with pharmaceutical components by mixing the components (e.g. pure or dissolved in a solvent such as water) with the polymer solution, after which the solvent is evaporated and/or freeze dried. Mixing is performed preferably with a turrax homogenizer.

Evidently, the possibilities are not limited to the above mentioned polymers but also other materials may be used, as long as they are synthetic, biodegradable and biocompatible and possess the desired mechanical, physicochemical and degradation properties. Polymers are the preferred materials, since they enable the design of drains having the desired properties (such as degradation behavior and mechanical properties) by selecting the proper synthesis conditions for the polymer.

The preferred biodegradable polymers used for drains according to the present invention, are those based on polyesters, polycarbonates, polyanhydrides, polyurethanes and/or polyamides, viz. the preferred biodegradable polymers comprise ester (—C(O)—O—), carbonate (—O—C(O)—O—), anhydride (—C(O)—O—C(O)—), urethane (—NH—C(O)—O—) and/or amide (—NH—C(O)—) groups. These polymers usually degrade through hydrolytic cleavage of the ester, carbonate or anhydride linkages. Enzymes or other bio-chemically active compounds may assist this hydrolytic cleavage and that of the urethane and amide bonds. The rate of degradation of the polymers can be regulated by choosing the content and combination of monomers.

Urethane and amide groups are usually present in combination with one or more of the polyester, polycarbonate or polyanhydride groups. The polyesters, polycarbonates or polyanhydrides without the presence of urethane or amide groups can either be homopolymers or copolymers. The copolymers can be random or can be block—or segmented copolymers.

In case the biodegradable polymer has a phase separated morphology, a first block is based on the polyesters, polycarbonates and/or polyanhydrides mentioned above. This first block is also referred to as the "soft" block and is amorphous with a glass transition temperature below mammalian body temperature at physiological conditions. The other (second) block or segment forms a crystalline hard block at these conditions such as urethane, amide, or it contains a polyester- or polyanhydride which is either crystalline or amorphous and having a phase transition larger than 37° C. (melting temperature or Tg).

The biodegradable polymer can also be combined with hydrophilic polymers, such as polyethers, polyvinylalcohol, polyvinylpyrrolidone or poly(hydroxymethylmethacrylate) (poly-(HEMA)). This means that the above-mentioned (co-)polymer chains are chemically combined with these hydrophilic polymers, e.g. by choosing synthesis conditions that allow incorporation of the hydrophilic polymers in the backbone or in the side-chain of the resulting copolymer. The hydrophilic polymer is preferably a polyether, more preferably a polyethyleneglycol. Other suitable polyethers are polytetramethyleneoxide (PTMO) and copolymers of e.g. polyethyleneglycol and polypropyleneglycol. The preferred molecular weight and amount of the polyethers is dependent on the hydrophilic properties that are demanded by the product. The polyethers can be mixed or can be a pre-polymer in combination with the biodegradable (pre)polymer.

The relative amounts of components must be chosen in such a way that a product with the desired physicochemical, thermal, mechanical, hydrophilic and degradation properties is obtained.

A drain for the above mentioned applications must be flexible, pliable and elastic. These properties can be obtained by using an appropriate processing method. For example, by winding of polymeric fibers into a coiled spring structure or by knitting or weaving of fibers, an open structured tube with above mentioned properties can be obtained, optionally followed by a dip-coating run to close the openings. Preferably, the drain is obtained by dip-coating or spray coating of a polymer solution on a mandrel or extrusion of a polymer. A solid tube is then obtained, after which perforations or carvings can be made.

By using a material with at least one softening point (Tg) equal to or below mammalian body temperatures (typically 37° C. for humans, but this may be higher, for instance in case of fever, when it may be as high as 41° C.) according to the present invention, drains are obtained, which have suitable elastomeric properties when placed in the body. The term softening point (Tg) as used herein, is defined herein as the first inflection point in a DSC (Differential Scanning Calorimetry) curve starting from low temperature upwards. It is to be understood that Tg refers to the Tg of a material when applied in vivo; viz. when at equilibrium with an atmosphere that is saturated with water vapor and at body temperature. Thus the materials of the present invention and the fact that at body conditions they have at least one softening point (glass transition temperature) of at most mammalian body temperature is reflected by the fact that these materials are flexible and preferably also elastic when applied at these body conditions. Alternatively, (in vitro) DSC measurement may be performed on the material after allowing the material to equilibrate with a water-saturated atmosphere at mammalian body temperature (typically this takes several minutes to one hour or more, such as 5 minutes or 30 minutes to 2 hour, or even to one day). When in dry state, the materials used in the present invention may have Tg values that are somewhat higher than mammalian body temperature, that is to say, when the dry materials are subjected to DSC, the first inflection point may arise at higher temperatures, for instance at 42 or 50° C., or more. Upon application in vivo, however, the dry material's Tg will drop as a result of the absorption of water and this final Tg should be about body temperature or lower according to the present invention.

The physical cross-links that are required for the elastomeric properties can be formed by chain entanglements which are present in an amorphous, high molecular weight copolymer or, in case of a phase separated copolymer, by crystalline or high Tg segments with a melting or glass transition temperature higher than 37° C. Drains based on materials with chemical cross-links can be made when the prepolymer and cross-linking agent are mixed and reacted in a predetermined shape e.g. by reacting in a mould or extruding the mixture of reacting components.

It is preferred to make the drain in one piece from a thermoplastic elastomeric polymer by a dip-coating or spray coating process. In the dip-coating process, a mandrel, having the shape of the drain to be obtained and which thus functions as the template for the drain, is submerged in a solution of the polymer (usually an organic solvent). After the mandrel is removed from the solution, a layer of solution remains adhered to its outer surface. Subsequently the solvent is evaporated. Optionally the procedure may be repeated to obtain drains having a higher wall thickness. In the spray-coating process, a polymer solution is sprayed on the rotating mandrel after which the solvent is evaporated. Several layers can be sprayed on the mandrel to obtain the desired thickness of the drain. Drains with various dimensions can be made in this way, depending on the dimensions of the mandrel. The thickness of the drain can be regulated by the number of dip- or spray cycles. Also, the drain can be made by extrusion. In this case, the polymer should be thermally stable, should not contain chemical cross-links and should not have a too high melting temperature or melt viscosity.

A biodegradable drain made of a synthetic polymer is preferably a flexible solid tube (with or without perforations) with an elastic modulus varying from 1-120 MPa. More preferably, and in particular for frontal sinus drains, the elastic modulus is 2-10 MPa. Drains have preferably a tensile strength of more than 2 MPa at an elongation at break of 500-1300%, more preferably the drains have a tensile strength of more than 5 MPa.

A polymeric material that fulfils all of the criteria will be a copolymer of lactide and ϵ-caprolactone. The lactide can be L, D or D,L-Lactide. The lactide content is preferably between 51-75%, because there is little or no swelling of the material with this composition. Too much swelling may lead to obstruction of the lumen so that drainage is prohibited. Most preferably, the lactide content is 62-69% and having a L/D ratio of 85/15 or 15/85. In case a racemic lactide is used, the molecular weight of the copolymer must be high enough to obtain a tube having the desired mechanical properties. The physical cross-links that give the material its elastic properties are caused by chain entanglements that can only be present if the molecular weight is high enough. An intrinsic viscosity (which is a measure for Mw) of at least 3 dl/g is very suitable in that case. In case an isomeric lactide or a lactide with an L/D ratio away from unity is used, physical cross-links can be obtained by poly-lactide sequences. The presence of long L- or D-lactide rich sequences increases the amount of physical cross-links. Maximum physical cross-linking is obtained with an isomeric lactide (either L or D). A lower molecular weight is then acceptable. In general, the intrinsic viscosity may vary from 1-6 dl/g. The time until the drain starts to loose its mechanical properties will be dependent on the starting molecular weight. A drain of a lactide-caprolactone copolymer material will keep its performing properties for preferably at least one week, more preferably about 2-12 weeks.

Another preferred embodiment is the use of segmented or block-copolymers comprising polyesters, polyester-carbonates or polyanhydrides. Preferably, these polymers have at least one Tg and one melting temperature or two separate Tg's within a copolymer, of which at least one transition occurs below 37° C. Also segmented or block copolymers with only one Tg below 37° C. of mixed phases are possible. Examples of the amorphous soft phase forming pre-polymers are those based on cyclic and/or non-cylic monomers such as lactide, glycolide, ϵ-caprolactone, δ-valerolactone, trimethylenecarbonate, tetramethylenecarbonate, 1,5-dioxepane-2-one, para-dioxanone and/or hydoxyalkanoic acid. The second or 'hard' phase may be formed by pre-polymers comprising poly-caprolactone, poly-valerolactone, poly-lactide, poly(lactide-glycolide), poly-para-dioxanone, poly(hydroxybutyricacid), polysebacic acid or poly(dodecanedioicanhydride) and combinations thereof. Combinations of these pre-polymers may also result in a segmented or block copolymer with a phase mixed morphology.

A suitable phase separated copolymer of this type is a DL-lactide-caprolactone copolymer with a lactide content of 20-40%. In this case, the ϵ-caprolactone content is high enough to crystallize. The amount of crystallization depends on the ϵ-caprolactone content and on the distribution of monomers. The monomers can be randomly distributed but preferably, the polymer is a segmented or block-copolymer with crystalline poly-caprolactone hard segments and amorphous poly(lactide-ϵ-caprolactone) soft segments. The general structure of these phase separated copolymers is $[-A-B]_n$ or ABA. n denotes the number of repeat units of -A-B- in case the segments A and B are alternating. $[-A-B-]_r$ is the notation for a multi-block segmented copolymer in which the segments A and B are randomly distributed and the ratio A/B is not necessarily equal to one. ABA is a triblock copolymer of segments A and B. A and B can be both the hard phase and soft phase forming segment, but can not be the same in one copolymer. The pre-polymer segments are preferably linked by an aliphatic diisocyanate, more preferably 1,4-butanediisocyanate. The crystallization of poly-caprolactone segments will yield a copolymer with a phase separated morphology, which will result in thermoplastic elastomeric properties. Block copolymers with structure ABA can also be chain-extended with an aliphatic multi-functional molecule. A polymer with a structure $[-ABA-]_n$ is then obtained.

By using this synthesis route the molecular sequence of a copolymer can be controlled as desired for a particular application. A drain made of this material may keep its performing properties for several months, depending on its composition. Materials with better mechanical and thermal properties than of random copolymers of (50/50) DL lactide and ϵ-caprolactone or lactide-caprolactone copolymers with a major lactide content, i.e. more than 50%, may be obtained. An elastic modulus of more than 10 MPa can be obtained and a tensile strength of more than 5 MPa.

An amorphous drain of a segmented polyester can be obtained when at least two different amorphous pre-polymers are chain-extended. Preferred are a combination of poly(DL-lactide) and poly(glycolide-lactide) chain-extended with 1,4-butanediisocyanate. The pre-polymer composition and ratio can be chosen in such a way to obtain a polymer with either one or two values of Tg. One of the amorphous pre-polymers may be initiated with a polyethyleneglycol (PEG). In this way, the hydrophilicity and rate of degradation can be influenced.

Another preferred embodiment is the use of biodegradable poly-urethanes for drains. The polymer is built of alternating polyester, polyether and/or polycarbonate containing soft segments and urethane hard segments, giving a phase separated structure. Polymers with very good mechanical properties can thus be obtained. Preferably, the urethane hard segments have a uniform block length which can be obtained by different chain-extending methods. A polymer with the highest degree of phase separation may be obtained by chain-extending the pre-polymer (hydroxyl terminated in case the initiator is a diol) with a diisocyanate chain-extender. Diisocyanate chain-extenders that are suitable for obtaining polymers with uniform hard segments and with sufficient mechanical properties are e.g. diisocyanate end-capped diol components, obtained by the reaction product of the diol with two equivalents of the diisocyanate. The diisocyanate is preferably 1,4-butanediisocyanate; the diol is preferably a linear aliphatic diol or a poly)ethylene glycol with general structure HO—$(CH_2)$n-OH with n=2-8 or HO—$(CH_2CH_2$—O)n-H with n=1-8, respectively. Even more preferably, the diol is a reaction product of two moles of these linear aliphatic diols or (poly)ethylene glycols with a diisocyanate, preferably 1,4-butanediisocyanate (obtainable by reacting the diisocyanate with an excess of the diol).

The phase separated segmented polyurethane can also be obtained by a method in which the di-hydroxy terminated pre-polymer is reacted with an excess of a diisocyanate, resulting in an isocyanate end-capped pre-polymer. Subsequently chain-extending with a diol compound or a reaction product of two equivalents of the diol with a diisocyanate will give a phase separated polyurethane with uniform block length. As diol compounds the above-mentioned linear aliphatic diol or (poly)ethylene glycol compounds may be used and preferably the above-mentioned reaction product of these diols with a diisocyanate are used. The degree of phase separation may in some cases be somewhat less than obtained with the first given chain-extending method. This is the result of trans-esterification reactions of labile ester groups. The polyester soft segment is a pre-polymer build of (mixtures of) monomers such as lactide (L,D or L/D), glycolide, ε-caprolactone, δ-valerolactone, trimethylene carbonate, tetramethylenecarbonate, 1,5-dioxepane-2-one or para-dioxanone. Optionally, polyethers are added to the polyester or polycarbonate pre-polymers, either as an initiator or as a second pre-polymer. The preferred polyurethane is composed of a poly(ether)ester pre-polymer soft segment and a polyurethane hard segment with a structure -BDI-BDO-BDI-BDO-BDI-(BDI being 1,4-butanediisocyanate and BDO being 1,4-butanediol). The preferred polyether is a polyethyleneglycol. The rate of degradation of the polyurethane will depend on the initial molecular weight (measured by the intrinsic viscosity) and the chemical composition of the pre-polymer.

The drains of the present invention are exceptionally suitable for application in the digestive channel in combination with interventions such as coloanal or esophagus anastomoses. For this type of application, the necessary physicochemical and mechanical properties are preferably retained from approximately 3 days to 6 weeks. The required degradation properties may be obtained (under the applied conditions) according to the present invention by choosing the chemical composition of the polymer. For application in coloanal anastomoses the polymer used in the present invention is preferably a poly(ether)-esterurethane. The pre-polymer for this application is preferably based on DL-lactide and ε-caprolactone and having a molecular weight of preferably 1500-2300, more preferably 2000 and may be obtained by a ring opening polymerisation initiated by 1,4-butanediol combined with the polyether compound. The preferred monomer ratio is from 50/50 to 70/30 (mol/mol). The PEG content in the polyurethane is preferably between 1-25 wt. % for applications in the digestive tract, more preferably from 5 to 20 wt. %. In particular, for coloanal anastomosis the PEG content is preferably between 2-10 wt. %. The molecular weight of PEG is preferably between 600-1500 and is most preferably 1000. Phase separated polyurethanes with molecular weights of the pre-polymer of 2000 may have an initial elastic modulus varying from 30-120 MPa and a tensile strength of 10-45 MPa. The elongation at break varies from 500-1200%.

The mechanical and degradation properties of the drains can easily be tuned by using a physical blend of suitable polymers. For example, a polyurethane can be blended with a copolymer giving a material with intermediate properties of the components. Preferably, the soft segment pre-polymer of the polyurethane is compatible (miscible) with the copolymer. A DL-lactide-ε-caprolactone based polyurethane is very well miscible with a lactide-caprolactone copolymer, due to the miscibility of the copolymer and pre-polymer soft segment. Drains that need to be kept in place for a much longer period of time before loosing the necessary physicochemical and mechanical properties, such as drains for the mid ear which may require to be put in place for a time of 6 to 9 months, are preferably made of polyesters, polycarbonates, polyurethanes, poly-anhydrides, polyamides or other polymers with slowly hydrolysable groups. The polyester or polycarbonate segments need to be build of slowly degrading monomers such as ε-caprolactone, δ-valerolactone, trimethylenecarbonate, tetramethylenecarbonate, para-dioxanone. Optionally, polyethers can be added.

EXAMPLES

Analysis Methods and Characterization of Copolymers

The following analysis methods were used in all examples, unless indicated otherwise.

The intrinsic viscosity ([η]), expressed in dl/g, was measured in chloroform at 25° C. using an Ubbelohde viscometer (according to ISO standard 1628-1).

Monomer conversion and copolymer composition were determined using $^1$H-NMR at 300 MHz in solutions in deuterated chloroform.

Thermal properties of polymers were determined using a TA Instruments-Q1000 MDSC, 5-10 mg samples being heated at a rate of 10° C. per minute, cooled down at a rate of 20° C. per minute and heated again at a rate of 10° C. per minute. The purity and melting point of the chain-extender (BDOBDIBDO) is measured according to ASTM E-928 method. Calculations are performed with Universal Analysis program (3.4C) of TA Instruments.

Purification and/or drying of monomers and glassware was carried out in accordance with previously published methods and was sufficient to obtain polymers with the desired properties.

Determination of Mechanical Properties of Drains:

The stress strain behavior of straight tubular drains was determined with an Instron 4301 tensile tester. The tubes were measured at room temperature at a crosshead speed of 10 mm/minute. The ultimate tensile strength, the elongation at break and the initial modulus were determined from these measurements.

Example 1

Synthesis of 65:35 (85/15)L/D Lactide-ε-caprolactone

DL-Lactide and L-Lactide (ratio 70:30) (Purac, the Netherlands) were introduced into a reaction vessel under nitrogen atmosphere and were dried in vacuum at 45° C. for at least 8 hours. ε-Caprolactone (Acros, Belgium) is dried over $CaH_2$ and distilled under reduced pressure in a nitrogen atmosphere.

Glass ampoules were covered inside with a teflon sheet (fluortec) and dried in an oven during one night. ε-Caprolactone was added to the lactide in the vessel in a monomer ratio 62/38 mol/mol (lactide/ε-caprolactone). The catalyst was added in an amount of $1 \times 10^{-4}$ mole of catalyst per mole of monomer. After 20 minutes of homogenisation at 120° C. the mixture was poured into the glass ampoules under nitrogen flow, after which the ampoules were closed with a stop. The ampoules were placed at 110° C. for 312 hours (13 days). The intrinsic viscosity was 6.2 dl/g. The monomer conversion was 95%. The lactide content in the polymer (calculated by NMR) was 65%. The glass transition temperature was 14.6° C.

Example 2 poly(DL-Lactide-ε-caprolactone) Prepolymer (Mn=2000)

The pre-polymer was synthesized by ring opening polymerization of ε-caprolactone and (50/50) DL lactide in a 50/50 (mol/mol) ratio using 1,4-butanediol as initiator and stannous octoate as catalyst. After reaction at 130° C. for 5 days, $^1$H-NMR showed complete monomer conversion.

Example 3

ε-Caprolactone Prepolymer (Mn=2000, 3000 and 4000)

The pre-polymer was synthesized by ring opening polymerization of ε-caprolactone using the appropriate amount of 1,4-butanediol as initiator and stannous octoate as catalyst. After reaction at 130° C. for 5 days, $^1$H-NMR showed complete monomer conversion.

Example 4 poly(DL-Lactide-ε-caprolactone) Pre-polymer (Mn=2000) Containing 13 wt. % PEG1000

The pre-polymer was synthesized by ring opening polymerization of (50/50) DL-lactide and ε-caprolactone in a 65/35 (mol/mol) ratio using the appropriate amount of 1,4-butanediol and PEG1000 as initiators and stannous octoate as catalyst. After reaction at 130° C. for 8 days, $^1$H-NMR showed complete monomer conversion.

Example 5

Synthesis of Segmented Co-polyesters with Randomly Distributed Segments: P(CL-DLLA): poly(caprolactone-DL-lactide)

Poly-caprolactone pre-polymers with Mn=2000, 3000 or 4000 of Example 3 and DL-lactide-ε-caprolactone (50:50) pre-polymer of Example 2 were weighed in the appropriate amounts into a glass ampoule supplied with nitrogen inlet and a mechanical stirrer. 1 equivalent of 1,4-butanediisocyanate (Bayer, distilled at reduced pressure) was added. The contents of the ampoule were quickly heated to 65° C. and then stirred mechanically for 15 minutes. As the mixture became viscous, the temperature was increased to 80° C. Stirring was stopped when the mixture became too viscous and the heating was continued for a maximum of 24 hours.

De ampoule was cooled to room temperature and the contents were isolated by dissolving the polymer in chloroform. The solution was filtered and poured into a petri-dish. The solvent was evaporated and after that the polymer film was dried in a vacuum oven at 40° C. In another method, the polymer solution was precipitated in ethanol or other suitable organic solvent, after which the polymer was isolated and dried.

Polymer composition is determined by $^1$H-NMR. The intrinsic viscosity varied from 1-4 dl/g. The glass transition temperatures of the copolymers varied from −14° C. to −27° C.; the melting temperatures of the crystalline phase was between 39° C. and 60° C., Generally, the higher the ε-caprolactone content and ε-caprolactone pre-polymer length, the higher the melting temperature and energy. In Table 1 the thermal properties of a few segmented polyesters are shown. The intrinsic viscosities of these specific copolymers were between 1.2 and 2 dl/g.

Example 6

Synthesis of 10 wt. % PEG Containing Polyurethane with BDI-BDO-BDI-BDO-BDI Hard Segment and PEG1000 and BDO Initiated (65/35) (DL-lactide-ε-caprolactone) Pre-Polymer Soft Segment A pre-polymer was prepared according to the method of Example 4. A reaction product of two molecules of butanediol (BDO) with 1,4-butanediisocyanate (BDI) was used as chain-extender (BDO-BDI-BDO). The preparation was carried out according to the method given in international application PCT/NL99/00352. The chain-extender was subsequently purified, such that a purity of at least 97% was obtained. The melting point of the chain-extender was 98° C.

In the first step of the polyurethane synthesis, the hydroxyl terminated pre-polymer was end-capped with a 5 to 6 fold excess of 1,4-butanediisocyanate under mechanical stirring. After reaction at 60° C. for 4 hours the excess BDI was removed by distillation under reduced pressure.

In the next step of the polymerization, the macrodiisocyanate was chain extended at 65° C. with the BDO-BDI-BDO chain extender using 1,4-dioxane as solvent (40% w/w). The chain-extender was added in small portions to the well stirred pre-polymer solution. When the solution became more viscous, the mixture was diluted with small amounts of dioxane. When the viscosity did not increase anymore, the solution was diluted with dioxane to the desired concentration. The polymer solution was frozen after which it was freeze dried. The solution can also be precipitated in water or organic solvents or it can be concentrated by evaporation and dried in vacuum. The polyurethane had an intrinsic viscosity of 1, 1 dl/g. The obtained polyurethane can be processed into a drain according to the methods of Example 7 and 10.

Example 7

Preparation of Drains according to FIGS. 1, 2 by a Dip-Coating Technique

General Method:

Drains were prepared of a polymer solution in chloroform or another organic solvent by dip-coating a straight tubular shaped mandrel or a mandrel with a funnel shape at one end with this solution, giving drains with the dimensions and shape of those of FIGS. 1 and 2, respectively. After dipping, the mandrel was placed horizontally and the solvent was allowed to evaporate during 5 minutes while rotating. This procedure was repeated until the desired wall thickness was obtained. The mandrel with the copolymer layer was placed first in ethanol and after that in distilled water. The tubes were removed from the mandrel and were cut into the appropriate size. They were placed in ethanol, followed by vacuum drying at 40° C. in order to remove any monomer- and low molecular weight residues and organic solvents.

Example 8

Preparation of a Drain of 65:35 (85/15)L/D Lactide-ε-caprolactone Copolymer

Drains of a copolymer of Example 1 were prepared according to the general method of Example 7. Mechanical properties of a 30 mm straight tube (without the funnel) part were measured: the initial modulus was 2.9 MPa, the stress at 400% strain was 3.3 MPa, the stress at break was 20 MPa and the strain at break was 750%.

Example 9

Preparation of Drains from Segmented Polyesters

Drains of multi-block segmented copolymers of Example 5 (polyesters build of poly-caprolactone and poly-(50/50) lactide-ε-caprolactone prepolymers with various ε-caprolactone/lactide ratios and with different pre-polymer lengths)

were prepared according to the general method of Example 7. The thermal- and mechanical properties of tubes with different composition are measured. The results are presented in Tables 1 and 2, respectively:

TABLE 1

Thermal properties of different phase separated poly(DL-lactide-ε-caprolactone prepolymers.

| % PCL prepolymer | Tg (° C.) | Tm (° C.) | ΔH (J/g) |
|---|---|---|---|
| 33 (Mn = 3000) | −16.8 | 49.0 | 26.7 |
| 40 (Mn = 3000) | −17.1 | 57.7 | 32.1 |
| 50 (Mn = 2000) | −23.1 | 53.3 | 27.1 |

TABLE 2

Mechanical properties of different phase separated poly(DL-lactide-ε-caprolactone prepolymers.

| % PCL prepolymer | Modulus (MPa) | Elongation at break (%) | Stress at break (MPa) |
|---|---|---|---|
| 33 (Mn = 3000) | 19.5 | 1220 | 15.1 |
| 40 (Mn = 3000) | 42.1 | 1330 | 13.4 |
| 50 (Mn = 2000) | 31.1 | 860 | 8.3 |

Example 10

Preparation of Drains of Polyurethanes by Dip-Coating

Drains of a polyurethane prepared according to the method of Example 6 and with a (50/50) poly(DL-lactide-ε-caprolactone) pre-polymer without PEG were prepared according to the general method of Example 7. Mechanical properties of a 30 mm straight tube (without the funnel) part were measured: the initial modulus was 35 MPa, the stress at 400% strain was 16 MPa, the stress at break was 41 MPa and the strain at break was 1000%.

Example 11

Preparation of Polyurethane Drains by a Spray-Coating Technique

Drains of a polyurethane of Example 6 were prepared by a spray-coating technique. A 4% solution of polyurethane in chloroform was sprayed on a horizontally rotating glass mandrel with a diameter of 36 mm. The polymer layer was dried where after the next layers are sprayed until the desired thickness is obtained. A drain with a diameter of 36 mm and a wall thickness between 70 and 150 μm was obtained. Drains are removed from the mandrel by a similar method as the dip-coated drains.

Example 12

Preparation of a Drain of 68:32 (85/15)L/D Lactide-ε-caprolactone Copolymer and DL-lactide-ε-caprolactone Based Polyurethane Drains of a blend of a 68:32 (85/15) L/D-Lactide-caprolactone copolymer and a (50/50) poly(DL-lactide-ε-caprolactone) based polyurethane made according to the method of example 6 were prepared according to the general method of Example 7. A 50:50 (w/w) mixture of the polymers was dissolved in chloroform. Mechanical properties of a 30 mm straight tube (without the funnel) part were measured: the initial modulus was 10 MPa, the stress at 400% strain was 6.7 MPa, the stress at break was 26 MPa and the strain at break was 990%.

The invention claimed is:

1. Drain suitable for draining a human or animal antrum, organ or tissue, characterized in that it comprises an elastic biocompatible, biodegradable synthetic thermoplastic non-chemically-crosslinked polymer, which polymer has at least one softening point of at most mammalian body temperature and an elastic modulus of up to 120 MPa,
wherein the biodegradable polymer comprises at least one of a polyester, polycarbonate, polyester-carbonate, polyanhydride, polyurethane or polyamide which are optionally combined with polyether groups,
wherein the polyester is a random DL-Lactide-ε-caprolactone copolyester, having a lactide content of 20-75 mol % and
the optional polyether is polyethyleneglycol, polypropyleneglycol, copolymers of polyethyleneglycol and polypropyleneglycol or polytetramethyleneoxide (PTMO).

2. Drain according to claim 1, consisting essentially of said synthetic biodegradable polymer.

3. Drain according to claim 1, wherein the polymer has at least one softening point (glass transition temperature) of at most 37-° C.

4. Drain according to claim 1, wherein the fraction of the L-enantiomer or the D-enantiomer of the lactide is from 65-95 mol.

5. Drain according to claim 1, wherein the polyester, polyester-carbonate and/or polyanhydride is a segmented or block copolymer with randomly or alternating segments or blocks and consisting of at least two blocks with different composition.

6. Drain according to claim 5, wherein the segments or blocks are phase separated hard and soft segments, characterized by at least two phase transitions, one of them being a glass transition temperature lower than 37-° C., the other a glass transition temperature or melting temperature higher than 37-° C.

7. Drain according to claim 5, wherein the segments or blocks forming the low temperature transition phase are composed of pre-polymers of or mixtures of cyclic or non-cyclic monomers lactide, glycolide, ε-caprolactone, δ-valerolactone, trimethylenecarbonate, tetramethylenecarbonate, 1,5-dioxepane-2-one, para-dioxanone and/or hydroxyalkanoicacid.

8. Drain according to claim 5, wherein the copolymer or pre-polymers are obtained by a ring opening polymerization initiated by a diol or di-acid compound.

9. Drain according to claim 5, wherein the pre-polymers forming the segments are linked by a difunctional aliphatic compound, preferably a diisocyanate, more preferably 1,4-butanediisocyanate.

10. Drain according to claim 6, wherein the hard segment or block is selected from the group consisting of poly-caprolactone, poly-valerolactone, poly-lactide, poly(lactide-glycolide), poly-para-dioxanone, poly (hydroxybutyricacid), polysebacic acid, poly(dodecanedioicanhydride) pre-polymers, and combinations thereof.

11. Drain according to claim 1, wherein said polymer is loaded with radiopaque fillers or pharmaceutical components comprising antibiotics, anti-inflammatory agents, peptides and proteins.

12. Drain according to claim 1, which is provided with perforations.

13. Nasal drain comprising an elastic biocompatible, biodegradable synthetic thermoplastic non-crosslinked polymer, wherein the polymer has at least one softening point of at most mammalian body temperature and an elastic modulus of up to 120 MPa,
- wherein the biodegradable polymer comprises at least one of a polyester, polycarbonate, polyester-carbonate, polyanhydride, polyurethane or polyamide which are optionally combined with polyether groups,
- wherein the polyester is a random DL-Lactide-ε-caprolactone copolyester, having a lactide content of 20-75 mol %, and
- the optional polyether is polyethyleneglycol, polypropyleneglycol, copolymers of polyethyleneglycol and polypropyleneglycol or polytetramethyleneoxide (PTMO).

14. Drain, being a nasal drain, according to claim 1, having a wall thickness of 0.05-5.0 mm.

15. Drain according to claim 1, having a total length of 3-300 mM.

16. Drain according to claim 1, having an outer diameter of 0.5-50 mm.

17. Drain according to claim 1, comprising a funnel shaped element on at least one end.

18. Drain according to claim 17, having a funnel length of 2-20 mm and a funnel diameter of 3-30 mm.

19. Drain according to claim 1, which is obtainable by dip-coating or spray coating of a polymer solution on a mandrel or extrusion of a polymer.

20. Method for treating a disorder associated with dysfunction of natural drainage of body fluids from an antrum, organ or tissue comprising introducing a drain according to claim 1 in said antrum, organ or tissue, such that said antrum, organ or tissue is connected with the environment or another location within the body, after which said drain degrades over time and degradation products of said drain are cleared through the digestive channel or said antrum, organ or tissue or absorbed and subsequently metabolized or secreted by the body.

21. Method according to claim 20, wherein said disorder is selected from (chronic) sinusitis, inflammation of the middle ear, liver disorders, disorders of the gastro-intestinal tract, tear duct disorder, surgical wound drainage, and thoracic disorder.

22. Method according to claim 20, wherein said drain is introduced in said antrum using at least one of a form of attachment selected from the group consisting of sealant, suture, and staple.

23. The method of claim 20, comprising performing coloanal anastomosis performing coloanal anastomosis.

* * * * *